US00PP36796P2

(12) United States Plant Patent
Bruinen

(10) Patent No.: US PP36,796 P2
(45) Date of Patent: Jul. 1, 2025

(54) ***ZAMIOCULCAS* PLANT NAMED 'EDZAM2202'**

(50) Latin Name: *Zamioculcas zamiifolia*
Varietal Denomination: EDZAM2202

(71) Applicant: Ed Holding B.V., Maasdijk (NL)

(72) Inventor: Ed Bruinen, Maasdijk (NL)

(73) Assignee: ED HOLDING B.V., Maasdijk (NL)

( * ) Notice: Subject to any disclaimer, the term of this patent is extended or adjusted under 35 U.S.C. 154(b) by 0 days.

(21) Appl. No.: 18/831,280

(22) Filed: Oct. 11, 2024

(51) Int. Cl.
*A01H 6/00* (2018.01)

(52) U.S. Cl.
USPC ..... Plt./373

(58) Field of Classification Search
USPC ..... Plt./373
CPC ..... A01H 6/00; A01H 5/00
See application file for complete search history.

*Primary Examiner* — Keith O. Robinson
(74) *Attorney, Agent, or Firm* — Samuel R. McCoy, Jr.

(57) ABSTRACT

'EDZAM2202' is a new and distinctive *Zamioculcas* plant which is characterized by a large plant size with light green juvenile leaflets which become progressively marbled with a dark green coloration until, ultimately, the mature-foliage becomes homogeneously dark green, and light yellow-green petioles with a combination of darker yellow-green and greyed-green blotches. The new plant propagates successfully by leaf cuttings and has shown to be uniform and stable in the resulting generations from asexual propagation.

2 Drawing Sheets

Latin name of the genus and species: The Latin name of the genus and species of the novel variety disclosed herein is *Zamioculcas zamiifolia* (hort. Lodd.) Engl.

Variety denomination: The inventive variety of *Zamioculcas* disclosed herein has been given the variety denomination 'EDZAM2202'.

BACKGROUND OF THE INVENTION

Parentage: 'EDZAM2202' is a seedling selection resulting from the controlled pollination of *Zamioculcas zamiifolia* 'CB5' (unpatented), the seed parent, with *Zamioculcas zamiifolia* 'AN3' (unpatented), the pollen parent, at a commercial nursery in Maasdijk, The Netherlands, in March of 2021. Both parents were developed and owned by the inventor and were never released to the public or otherwise made commercially available. In September of 2021, one plant was observed to exhibit unique foliage coloration characteristics and was isolated for further evaluation in order to confirm the distinctness and stability of the characteristics first observed. Upon confirmation of distinctness and stability, 'EDZAM2202' was selected for commercialization.

Asexual Reproduction: Asexual reproduction of 'EDZAM2202' was first accomplished in January of 2022 by way of stem cuttings at a commercial greenhouse in Maasdijk, The Netherlands. Two successive generations produced from stem cuttings have shown that the unique features of the instant cultivar are stable and reproduce true to type.

SUMMARY OF THE INVENTION

The cultivar 'EDZAM2202' has not been observed under all possible environmental conditions and the phenotype may vary somewhat with variations in the instant environment such as temperature, day length, and light intensity, without, however, any variance in genotype. The following characteristics have been repeatedly observed and represent the distinguishing characteristics of the new *Zamioculcas* plant, 'EDZAM2202'. These traits, in combination, distinguish 'EDZAM2202' as a new and distinct cultivar.

1. *Zamioculcas* 'EDZAM2202' exhibits a relatively large plant size; and
2. *Zamioculcas* 'EDZAM2202' exhibits an abundance of foliage; and
3. *Zamioculcas* 'EDZAM2202' exhibits light green juvenile leaflets which become progressively marbled with a dark green coloration until, ultimately, the mature foliage becomes homogeneously dark green; and
4. *Zamioculcas* 'EDZAM2202' exhibits light yellow-green petioles with a combination of darker yellow-green and greyed-green blotches.

BOTANICAL DESCRIPTION OF THE PLANT

Figure 1:
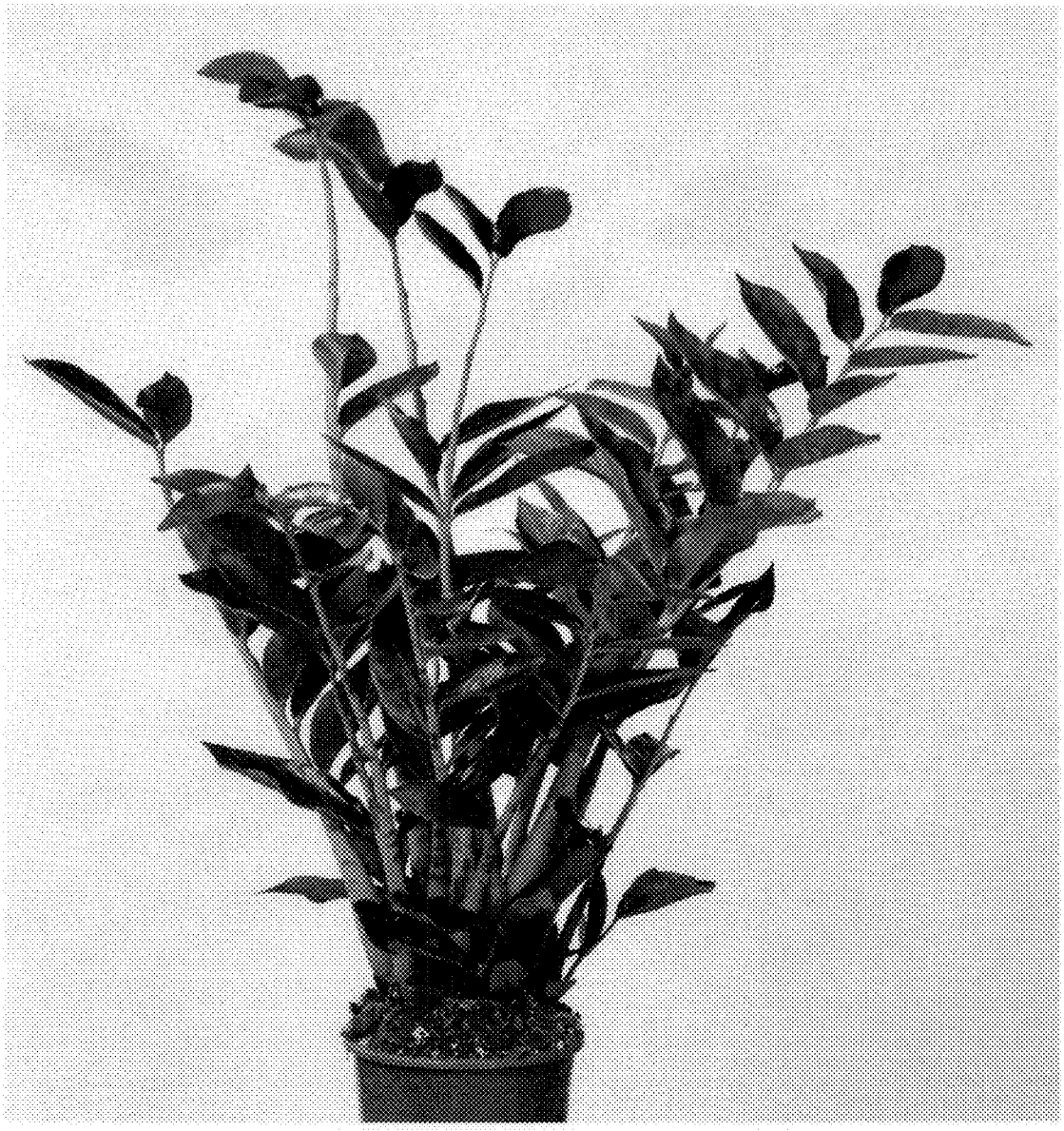
FIG. 1 shows, as nearly true as it is reasonably possible to make the same in color illustrations of this type, the typical foliage and growth characteristics of the new cultivar, 'EDZAM2202'. The plant shown is approximately 12 months old, potted into a 15 cm nursery pot, grown at a commercial greenhouse in Maasdijk, The Netherlands.
Figure 2:
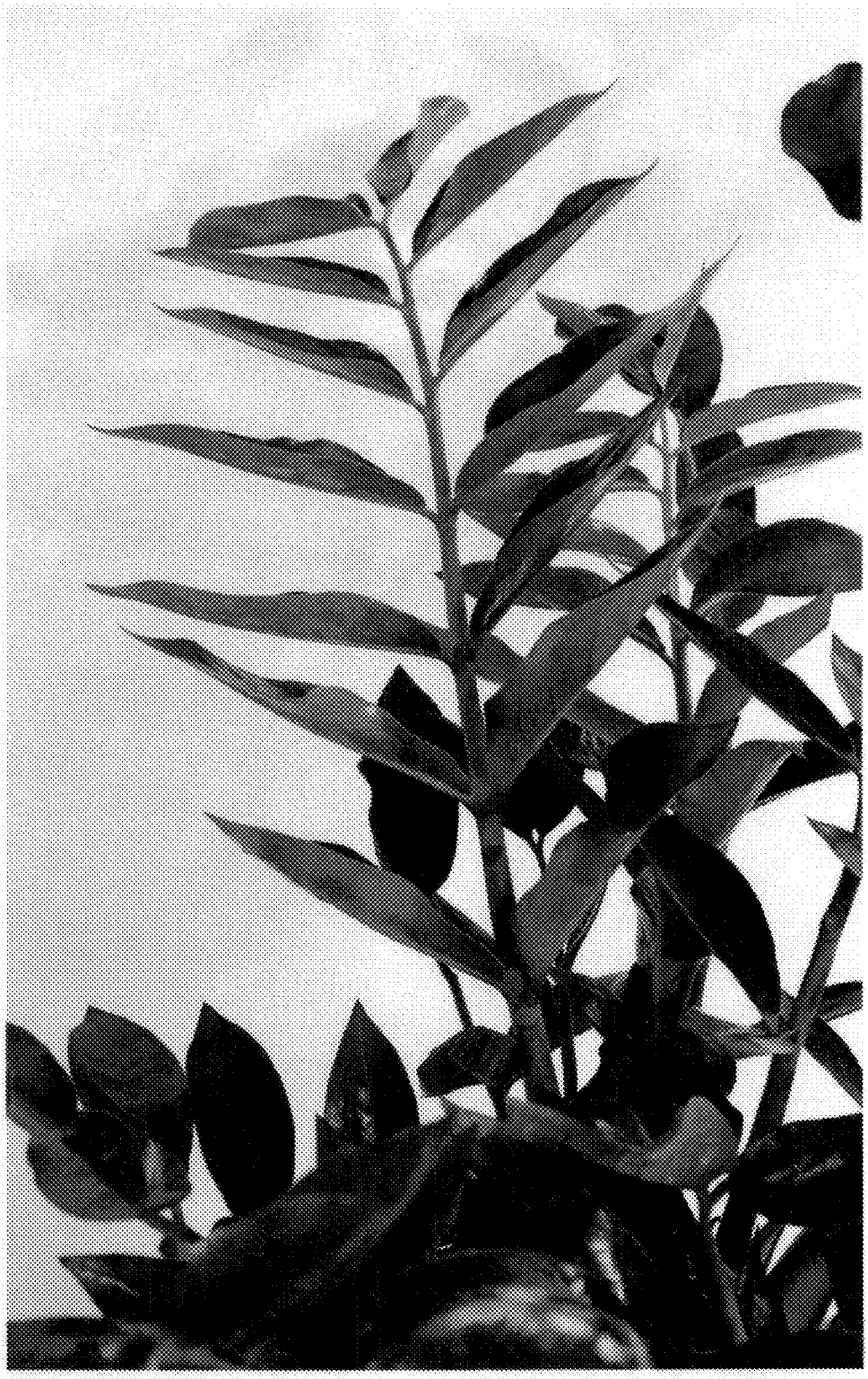
FIG. 2 shows, as nearly true as it is reasonably possible to make the same in color illustrations of this type, the typical foliage of the plant in FIG. 1.

The following is a detailed botanical description of a new and distinct variety of *Zamioculcas zamiifolia* known as 'EDZAM2202', based upon observations of 12-month-old plants, potted into 15 cm nursery pots and grown indoors at a commercial nursery in Maasdijk, The Netherlands. Plants were grown in full sun using accepted fertility, to include supplemental Calcium applications, and irrigation practices for *Zamioculcas* plants. With the exception of preventative fungicides, no chemical pest control measures were employed. Furthermore, no artificial light or photoperiodic treatments were given to the plants. Observation data was recorded in September of 2023.

Those skilled in the art will appreciate that certain characteristics will vary with older or, conversely, with younger plants. 'EDZAM2202' has not been observed under all possible environmental conditions. Where dimensions, sizes, colors and other characteristics are given, it is to be understood that such measurements are approximations or averages set forth as accurately as practicable. The phenotype of the variety may differ from the descriptions set forth herein with variations in environmental, climactic and cultural conditions. Color notations are based on *The Royal Horticultural Society Colour Chart*, The Royal Horticultural Society, London, sixth edition, 2015.

A botanical description of 'EDZAM2202' and comparisons with the parent plants and the most similar variety of common knowledge are provided below.

General plant description:

*Growth habit*.—Tropical evergreen perennial.

*Plant profile shape*.—Inverted triangular.

*Growth rate*.—Moderately fast to fast growing.

*Plant vigor*.—Moderately vigorous to highly vigorous.

*Height*.—68.8 cm to the top of the foliar plane.

*Width*.—66.0 cm.

*Propagation*.—Type — Leaf cuttings. Time to initiate rooting — Approximately 30 days at an approximate temperature of 25 degrees Celsius. Crop time — Approximately 1 year to produce a marketable plant in a 15 cm container.

*Pathogen and pest resistance and susceptibility*.—Plants have not been observed to be susceptible or resistant to pathogens and pests common to *Zamioculcas* sp.

*Environmental tolerances*.—Adapt to, at least, USDA Zones 10 to 12 and temperatures ranging from 5 to 40 degrees Celsius; moderate tolerance to rain; low tolerance to wind.

Stem:

*Branching habit*.—No stems or branches; compound leaves in small clumps, arising directly from tuberous rhizomes.

*Number of clumps per plant*.—Two, on average.

*Number of additional clumps formed each year*.—Seven, on average.

Root system:

*Type*.—Tuberous rhizomes bearing thick fleshy roots.

*Shape of rhizomes*.—Irregular broad oblong to ovoid.

*Dimensions of rhizomes*.—6.2 cm long and 3.5 cm in diameter.

*Density of rhizomes and roots*.—Moderately dense.

*Distribution of rhizomes and roots*.—Rhizomes shallow; roots distributed evenly throughout the soil profile, from shallow to deep.

*Texture of rhizomes and roots*.—Glabrous and very fleshy.

*Color of rhizomes and roots*.—Greyed-green, nearest to a mixture of RHS 195A, 195B, and 195C.

Foliage:

*Arrangement*.—Compound leaves in small clumps, arising directly from tuberous rhizomes.

*Attachment*.—Petiolate.

*Division*.—Pinnately compound.

*Leaf profile shape*.—Oblong.

*Dimensions*.—64.3 cm long and 23.1 cm wide.

*Attitude*.—Near upright; approximately 20 degrees from vertical.

*Quantity*.—Approximately 5 leaves per clump.

*Stipules*.—General — A leafy stipule is present at the base of each pinnately compound leaf. Shape — Lanceolate. Length — 18.4 cm. Width — 4.9 cm. Apex — Mucronulate. Base — Broad cuneate. Margin — Entire, moderately undulated. Texture — Papery. Color, adaxial surface — Translucent grey-brown, nearest to RHS 199B, and transitioning to a darker shade of greyed-brown towards the apex, nearest to RHS N199C. Color, abaxial surface — Grey-brown, nearest to RHS. N199D, and transitioning to a darker shade of greyed-brown towards the apex, nearest to RHS N199C.

*Petiole*.—Aspect — Terete; basal portion of the petiole swollen. Length — 58.1 cm, including the swollen portion of the petiole; the swollen portion is 15.8 cm long. Diameter — 3.6 cm at the base; 1.2 cm below the first leaflet. Strength — Strong. Texture — Smooth and glabrous. Luster — Matte. Color, adaxial and abaxial surfaces — Yellow-green, nearest to RHS 147B, and sparsely and irregularly blotched with a combination of yellow-green (RHS 148A), and a mixture of yellow-green and greyed-green (nearest to RHS 148A and 197B).

*Rachis*.—Aspect — Elliptic. Length — 58.1 cm, including the geniculum. Diameter — 1.4 cm at the widest point; 1.2 cm at the narrowest point. Strength — Strong. Texture — Smooth and glabrous. Luster — Matte. Color, adaxial surface — Greyed-green, nearest to a combination of RHS 194A, 194B, and 194C; sparsely and irregularly blotched with a combination of yellow-green (RHS 148A), and a mixture of yellow-green and greyed-green (nearest to RHS 148A and 197B). Color, abaxial surface — Greyed-green, nearest to a combination of RHS 194A, 194B, and 194C; irregularly blotched with a combination of yellow-green (RHS 148A), greyed-green (RHS N189B), and a mixture of yellow-green and greyed-green (nearest to RHS 148A, N189B, 197A, and 197B).

*Leaflets*.—Quantity — Typically 17 leaflets but ranging from 13 to 21. Attitude — At an angle of approximately 60 degrees to the rachis. Dimensions — 13.7 cm long and 5.0 cm wide. Shape — Elliptic to oblong. Aspect — Slightly carinate and lightly curled inward. Apex — Acute with a mucronulate tip. Base — Obtuse to broad attenuate. Margin — Entire; slightly undulated. Texture, adaxial surface — Glabrous and moderately coriaceous. Texture, abaxial surface — Glabrous and moderately coriaceous. Luster, adaxial surface — Glossy. Luster, abaxial surface — Glossy. Color — Juvenile foliage color, adaxial surface — Green, nearest to a mixture of RHS 137B and 143A yet darker. Juvenile foliage color, abaxial surface — Yellow-green, nearest to RHS 144A. Mature leaf color, adaxial surface — Greyed-green, nearest to RHS N189A, and suffused with black, nearest to RHS 203B. Mature leaf color, abaxial surface — Yellow-green, nearest to RHS 146A, and finely marbled with a darker shade of yellow-green, RHS 147A. Venation — Pattern — Pinnate. Vein color, adaxial surface — Green, nearest to RHS NN137B. Vein color, abaxial surface — Yellow-green, nearest to RHS 146B. Petiolule — Aspect — Flattened elliptic. Length — 0.6 cm. Diameter — Petioles flattened; average width is 0.40 cm and the average height is 0.35 cm. Strength — Strong. Texture, adaxial and abaxial surfaces — Smooth and glabrous. Luster, adaxial and abaxial surfaces — Matte. Color, adaxial surface — Yellow-green, nearest to RHS 146C. Color, abaxial surface — Yellow-green, nearest to RHS 146B.

Inflorescence: No flowering has been observed to date.

COMPARISON WITH THE PARENT PLANTS

Plants of the new cultivar 'EDZAM2202' may be distinguished from its seed parent, *Zamioculcas zamiifolia* 'CB5' (unpatented), by the characteristics described in Table 1.

TABLE 1

Comparison Between 'EDZAM2202' and The Seed Parent

| Characteristic | 'EDZAM2202' | 'CB5' |
|---|---|---|
| Foliage abundance. | Less abundant than the 'CB5' | More abundant than 'EDZAM2202' |
| Leaflet shape. | Elliptic to oblong. | Elliptic. |
| General coloration of the foliage. | Lighter shade of green compared to 'CB5' | Darker shade of green compared to 'EDZAM2202'. |

Plants of the new cultivar 'EDZAM2202' may be distinguished from its pollen parent, *Zamioculcas zamiifolia* 'AN3' (unpatented), by the characteristics described in Table 2.

TABLE 2

Comparison Between 'EDZAM2202' and The Pollen Parent

| Characteristic | 'EDZAM2202' | 'AN3' |
|---|---|---|
| Foliage abundance. | More abundant than 'AN3' | Less abundant than 'EDZAM2202' |

TABLE 2-continued

Comparison Between 'EDZAM2202' and The Pollen Parent

| Characteristic | 'EDZAM2202' | 'AN3' |
|---|---|---|
| Leaflet shape. | Elliptic to oblong. | Oblong. |
| General coloration of the foliage. | Darker shade of green compared to 'AN3'. | Lighter shade of green compared to 'EDZAM2202'. |

COMPARISONS WITH THE MOST SIMILAR VARIETY OF COMMON KNOWLEDGE

Plants of the new cultivar 'EDZAM2202' are most similar to the commercial variety, *Zamioculcas* 'EDZAM1702' (U.S. Plant Pat. No. 33,429). A comparison of 'EDZAM1701' with 'EDZAM1702' is described in Table 3.

TABLE 3

Comparison Between 'EDZAM2202' and 'EDZAM1702'

| Characteristic | 'EDZAM2202' | 'EDZAM1702' |
|---|---|---|
| Leaflet attitude. | More relaxed than 'EDZAM1702'. | More upright than 'EDZAM2202'. |
| Leaflet shape. | Elliptic to oblong. | Elliptic. |
| General coloration of the foliage. | Darker shade of green compared to 'EDZAM1702'. | Lighter shade of green compared to 'EDZAM2202'. |
| General coloration of mature petioles. | Yellow-green and sparsely and irregularly blotched with a combination of yellow-green and a mixture of yellow-green and greyed-green. | Solid yellow-green. |

That which is claimed is:

1. A new and distinct variety of *Zamioculcas* plant named 'EDZAM2202', substantially as described and Illustrated herein.

* * * * *